Feb. 26, 1974 F. BLOUNT Plant Pat. 3,496
APPLE TREE
Filed Oct. 26, 1972
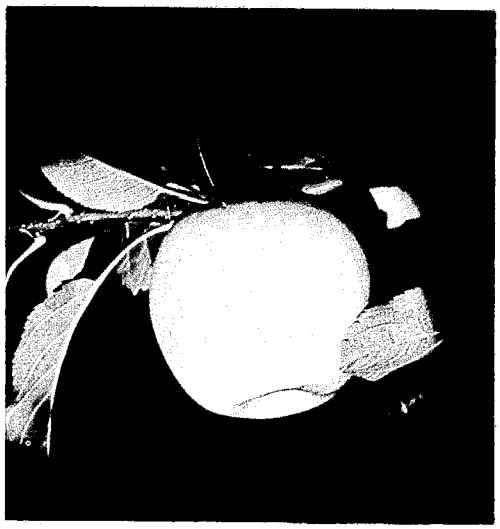
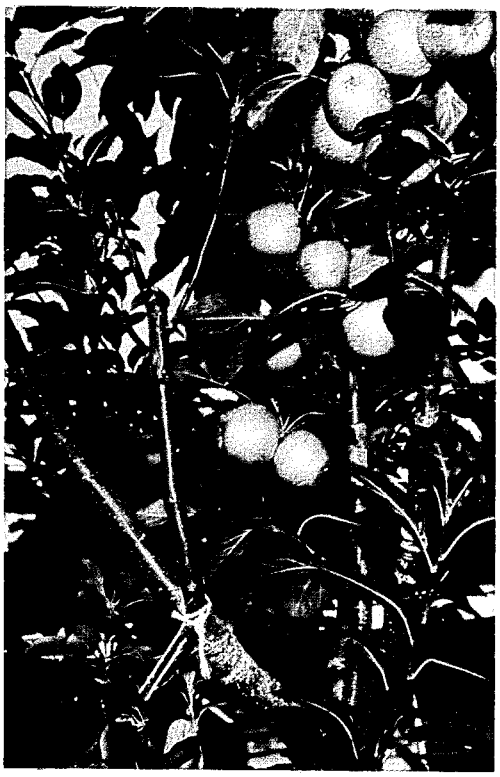
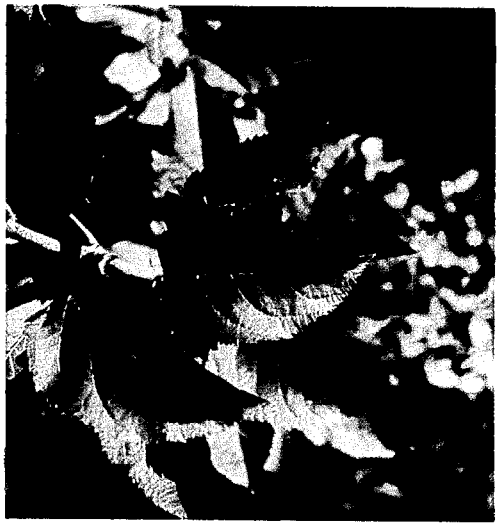

United States Patent Office

Plant Pat. 3,496
Patented Feb. 26, 1974

3,496
APPLE TREE

Floyd Blount, 10941 Beauty Lane, Dallas, Tex. 75229

Filed Oct. 26, 1972, Ser. No. 300,899
Int. Cl. A01h 5/03
U.S. Cl. Plt.—34 1 Claim

ABSTRACT OF THE DISCLOSURE

A new and distinct variety of apple tree of the golden delicious type which is more highly productive and at an earlier age than other varieties of golden delicious apple and which produces fruit of a size and quality superior to other varieties of golden delicious apple. The leaves which are unlike those of other apple varieties are arranged to give a good mix of shade and sun to withstand the hot summers of the Southwestern United States and are large, dark green, and leathery, with a tendency to have deeply serrated edges. The tree and fruit grow extremely well in the climate of the Southwestern United States and are particularly well adapted to the hot dry summers of Texas and Oklahoma. The fruit is more disease resistant than other varieties of golden delicious apple and is not course and pithy as are other golden delicious varieties grown in the Southwest United States.

The present invention relates to a new and distinct variety of apple tree which was discovered by me as a seedling of an unknown variety or golden delicious type of apple, the parent fruit having been obtained by me in Irving, Texas, and the seedling having been grown by me in Altus, Okla.

I originally selected seeds from several extra large golden delicious apples and brought a number of the seedlings to fruiting size at different locations. At the time of my discovery, my attention was particularly drawn to the variety of the subject invention because it appeared to be superior to all other varieties of yellow delicious apple with which I am familiar.

After my initial discovery of the superiority of the seedling over other varieties, I promptly took steps to preserve and propagate the same and asexual reproduction by grafting as performed by me in my yard in Dallas, Texas, and on my farm near Athens, Texas, accompanied by continued observations and testing of the new variety, have fully established that the distinctive characteristics come true to form and are established and transmissible through succeeding propagations.

My new variety is definitely distinguished from all other varieties of which I am aware, and the distinctive features thereof constitute substantial improvements over other varieties and represent exceedingly desirable characteristics from both a commercial and home orchard stand-point.

My new variety is more productive and at an earlier age than other varieties of golden delicious apple and produces fruit of a size and quality superior to other varieties. The leaves of my variety which are unlike those of other apple varieties are arranged on the tree to give a good mix of shade and sun to withstand the hot summers of the Southwestern United States and are large, dark green, and leathery, with a tendency to have deeply serrated edges. The tree grows and bears and the fruit matures extremely well in the climate of the Southwestern United States, and the variety is better adapted to the hot dry summers of Texas and Oklahoma than other varieties.

The limbs of my new variety are very strong and do not break with heavy loads. Also wind and scrape damage are nearly non-existent due to the positioning of the fruit on the limbs.

My new variety is disease resistant, shows no signs of scab, and is not as prone to russet as other varieties grown in the Southwest United States.

The tree of my variety is semi-spur type and bears clusters of fruit both along the limbs and on short twigs. The fruit is well shaped, type, very prolific and self pollinating and should be thinned to king blossom fruit for largest size as it tends to bear in clusters of five.

The fruit retains its firmness very well and improves its golden coloring in storage and is not pithy like other varieties of golden delicious apple grown in the Southwest United States.

The accompanying drawings show typical specimens of the foliage and fruit of my new variety, as well as the growth of a tree bearing unripe fruit, all as depicted in color as nearly true as it is reasonably possible to make the same in a color illustration of this character.

The following is a detailed description of my new variety with color terminology in accordance with Ridgway's Color Standards and Color Nomenclature, and with the Horticultural Color Chart of the British Color Council, as indicated, except where general color terms of ordinary dictionary significance are obvious:

Observations made from specimens grown in Dallas, Tex.

Dates first and last pickings: from about Aug. 15 to about Sept. 1.

Tree: Medium size; medium vigorous; upright; dense; inverted vase-formed; hardy; very productive; great heat tolerance; regular bearing.

*Trunk.*—Medium stocky; very smooth.

*Branches.*—Very thick; smooth; with many spurs.

*Twigs.*—Color—chestnut, Plate II, Color No. 9. Tone m (Ridgway). Lenticles—large number; large size; closely spaced on all size limbs.

*Leaves.*—Large size; medium width (about 2½ inches; extra long length (about 4½ to 5 inches); form—modified elliptical; taper—pointed; very thick; smooth; slightly rugose. Color—Ivy Green. Plate 000 1060/3, p. 200, Volume 2 (Horticultural Color Chart). Margin—coarsely serrate sometimes jagged. Petiole—medium length (about 1 inch); thick.

Flowers: Very early; medium

*Color.*—White, with tinge of Crimson, Plate 22/3, page 22, Volume 1( Horticultural Color Chart).

*Date of first bloom.*—Mar. 15.

*Date of full bloom.*—Mar. 23.

Fruit:

*Maturity when described.*—Eating ripe—138 days from full bloom.

*Size.*—Uniform. Axial diameter—about 3 inches.

*Transverse diameter.*—About 3 inches.

*Shape.*—Moderately conical; not ribbed.

*Cavity.*—Symmetrical; rounded toward apex; acute; undulate; not pubescent. Depth, shallow—about ½ inch.

*Breadth.*—About 1¼ inches.

*Markings.*—Some present near apex. Color—Buffy Brown, Plate XL, Color No. 17, tone i (Ridgway).

*Basin.*—Symmetrical; flaring base; wide; furrowed; mammiform. Depth—about ⅜ inch.

*Breadth.*—About 11/16 inch.

*Stem.*—Clubbed; slender, pubescent; about 13/16 inch long.

*Calyx.*—Slightly open; segments persistent; broadly lanceolate; acute; about 15/16 inch long; approximate at base; prostrate; reflexed from base at apex. Outer surface—Pubescent. Inner surface—pubescent.

*Eye.*—Small; partially closed.

*Skin.*—Thick; tough; smooth; waxed. Dots—obscure; few; small; insignificant; even; ruptured; angular; color—yellow ochre, Plate 07/3, page 101, Volume 2 (Horticultural Color Chart); distribution—uniform. Ground color—Barium yellow, Plate 503, page 131, Volume 2 (Horticultural Color Chart). Color markings—blushed; self-colored; bright; color—yellow ochre, Plate 07, page 101, Volume 2 (Horticultural Color Chart).

*Bloom.*—Wanting.

*Scarfskin.*—Wanting.

*General color effect.*—Light yellow all over.

*Flesh.*—Rather juicy. Color—Satiny white, with yellowish tint, yellow ochre, Plate 07/1, page 101, Volume 2 (Horticultural Color Chart) not in vascular bundles. Texture—firm; fine; crisp. Flavor—mild; rich. Aroma—distinct. Quality—best.

*Core.*—Median; distinct in cross-section; indistinct carpellary area. Bundle area—medium size; cordate; symmetrical at base; acute at base; in bundles opposite and alternate with cell. Halves of core—unequal. Bundle—inconspicuous; in one whorl; color—chartreuse green, Plate 663/1, page 90, Volume 1 (Horticultural Color Chart). Core lines—clasping. Calyx tube—glabrous toward base; broadly obconic; urn-shaped; depth of tube to shoulder about 3/16 inch; entire depth about 9/16 inch. Styles—present; distinct toward base; pubescent toward base. Stamens—in one distinct whorl; marginal. Axiallary cavity—present. Seed cells—axile; open. Cell walls—distant; thick; tough; length—about ½ inch; breadth—about ¼ inch. Longitudinal section—broadly oval; acute at apex. Cross section—broad. Surface—fissured.

Seeds:

*Number.*—5 perfect; 3 imperfect, 2 per cell.

*Length.*—About 5/16 inch.

*Breadth.*—About 5/32 inch.

*Form.*—Obtuse.

*Color.*—Chestnut, Plate II, Color No. 9, Tone m (Ridgway).

*Use.*—Market; dessert.

*Keeping quality.*—Good; about 30 days in ordinary storage.

I claim as my invention and desire to protect by Letters Patent of the United States:

1. A new and distinct variety of apple tree of the golden delicious type, substantially as herein shown and described, characterized particularly as to novelty by its general similarity to the trademarked variety "Starkspur Golden Delicious" but being distinguished therefrom by its greater productivity; its earlier-bearing habit, the greater size and quality of its fruit, the arrangement, size, texture, and form of its leaves, its ability to grow and bear well in the hot summer sun of the Southwest United States, its ability to resist diseases including russet and scab, its superior eating qualities, and the ability of its limbs to withstand heavy loads and wind and scrape damage.

No references cited.

ROBERT E. BAGWILL, Primary Examiner